(12) United States Patent
Doi et al.

(10) Patent No.: US 9,901,530 B2
(45) Date of Patent: Feb. 27, 2018

(54) OIL-IN-WATER EMULSION COMPOSITION AND COSMETICS

(71) Applicant: DAITO KASEI KOGYO CO., LTD., Osaka-shi, Osaka (JP)

(72) Inventors: Moeko Doi, Osaka (JP); Noboru Nagatani, Osaka (JP); Takumi Tanaka, Osaka (JP)

(73) Assignee: DAITO KASEI KOGYO CO., LTD., Osaka (JP)

( * ) Notice: Subject to any disclaimer, the term of this patent is extended or adjusted under 35 U.S.C. 154(b) by 0 days.

(21) Appl. No.: 15/317,112

(22) PCT Filed: Jul. 18, 2014

(86) PCT No.: PCT/JP2014/069207
§ 371 (c)(1),
(2) Date: Dec. 7, 2016

(87) PCT Pub. No.: WO2016/006119
PCT Pub. Date: Jan. 14, 2016

(65) Prior Publication Data
US 2017/0119652 A1    May 4, 2017

(30) Foreign Application Priority Data
Jul. 8, 2014    (JP) .................. 2014-140506

(51) Int. Cl.
| | |
|---|---|
| *A61K 8/85* | (2006.01) |
| *A61K 8/06* | (2006.01) |
| *A61Q 19/00* | (2006.01) |
| *A61Q 17/04* | (2006.01) |
| *A61Q 1/02* | (2006.01) |
| *C08J 3/12* | (2006.01) |

(52) U.S. Cl.
CPC ............... *A61K 8/85* (2013.01); *A61K 8/062* (2013.01); *A61Q 1/02* (2013.01); *A61Q 17/04* (2013.01); *A61Q 19/00* (2013.01); *C08J 3/12* (2013.01); *A61K 2800/33* (2013.01); *A61K 2800/412* (2013.01); *C08J 2367/04* (2013.01)

(58) Field of Classification Search
CPC .... A61K 9/0024; A61K 9/204; A61K 9/2095; A61K 8/85; A61K 2800/33; A61K 8/0241; A61K 8/0279; A61K 8/062; A61K 8/365; A61K 9/1647
See application file for complete search history.

(56) References Cited

U.S. PATENT DOCUMENTS

| | | |
|---|---|---|
| 5,643,555 A | 7/1997 | Collin et al. |
| 6,126,948 A | 10/2000 | Simonnet et al. |
| 6,258,345 B1 | 7/2001 | Rouquet et al. |
| 6,440,399 B1 | 8/2002 | Gers-Barlag et al. |
| 2001/0026811 A1 | 10/2001 | Rouquet et al. |
| 2002/0018789 A1 | 2/2002 | Gers-Barlag et al. |
| 2002/0102284 A1 | 8/2002 | Rouquet et al. |
| 2002/0127191 A1 | 9/2002 | Gers-Barlag et al. |
| 2003/0017184 A1 | 1/2003 | Gers-Barlag et al. |
| 2004/0146540 A1 | 7/2004 | Ueda et al. |
| 2013/0309497 A1 | 11/2013 | Takezaki et al. |
| 2015/0183928 A1 | 7/2015 | Takezaki et al. |

FOREIGN PATENT DOCUMENTS

| | | |
|---|---|---|
| JP | 2656226 B2 | 9/1997 |
| JP | 11158030 A | 6/1999 |
| JP | 2001518111 A | 10/2001 |
| JP | 2006036763 A | 2/2006 |
| JP | 2007332037 A | 12/2007 |
| JP | 2009161460 A | 7/2009 |
| WO | 02100357 A1 | 12/2002 |
| WO | 2012105140 A1 | 8/2012 |

OTHER PUBLICATIONS

B. Binks, et al., "Emulsions Stabilised Solely by Colloidal Particles", Advances in Colloid and Interface Science, 100-102 (2003), pp. 503-546.
B Binks, et al., Advances in Colloid and Interface Science, 100-102 (2003).
C. Whitby, et al., "Poly(lactic-co-glycolic acid) as a particulate emulsifier", Journal of Colloid and Interface Science, Jun. 1, 2012, vol. 375, No. 1, pp. 142-147.
International Search Report (ISR) and Written Opinion dated Sep. 16, 2014 issued in International Application No. PCT/JP2014/069207.
Extended European Search Report (EESR) dated Nov. 23, 2017 issued in counterpart European Application No. 14897233.4.

*Primary Examiner* — Nannette Holloman
(74) *Attorney, Agent, or Firm* — Holtz, Holtz & Volek PC

(57) ABSTRACT

The present invention provides, without use of a surfactant, an oil-in-water emulsion composition and cosmetics having fresh and smooth feeling without powderiness in use, and having excellent emulsion stability by preparing a Pickering emulsion using a spherical polylactic acid powder. An oil-in-water emulsion composition is obtained as a composition containing (a) a spherical polylactic acid powder having an average particle size of from 0.5 to 1.5 μm, wherein 90% or more by volume of the whole particles of the powder have a particle size of 3 μm or less, (b) an oil phase component, and (c) an aqueous phase component, and containing substantially no surfactant. Desired cosmetics are obtained by using the oil-in-water emulsion composition.

8 Claims, 1 Drawing Sheet

OIL-IN-WATER EMULSION COMPOSITION AND COSMETICS

TECHNICAL FIELD

The present invention relates to an oil-in-water emulsion composition and cosmetics, and specifically relates to an oil-in-water emulsion composition and cosmetics having fresh and smooth feeling without powderiness in use, and having excellent emulsion stability, that contains no surfactant as a result of use of a spherical polylactic acid powder.

BACKGROUND ART

In an emulsion composition used in cosmetics and the like, an aqueous component and an oil-based component are stably mixed by emulsifying action of a surfactant contained in the composition.

However, a surfactant is a highly sticky material, and thus, as far as possible, reduction or exclusion of a surfactant is desired for preparing cosmetics having favorable feeling in use.

Under the above circumstances, various trials have been made to produce an emulsion composition without using a surfactant.

In the early 1900s, it was reported that mixing of powder particles or colloidal particles into two mutually immiscible liquids leads to adsorption of the particles onto the interface of the liquids, which resulted in stabilization of the resultant emulsion system. The emulsion produced by this method is referred to as a Pickering emulsion, and is widely used in various natural and industrial processes (see Non-Patent Literature 1). An application of the Pickering emulsion is also proposed in the cosmetic field. However, various restrictions (such as, size, noncohesiveness, and wettability) are imposed on available powders and colloidal particles, which leads to limitation of types of powders and colloidal particles applicable to cosmetics (see Patent Literatures 1 to 3).

Inorganic powder particles used in the Pickering emulsion (e.g., Patent Literature 1: polyalkyl silasesquioxane particles, Patent Literature 2: a metal oxide, Patent Literature 3: silica/titanium dioxide/zinc oxide, Patent Literature 4: an inorganic powder) generally have an emulsifying ability inferior to that of a surfactant widely used in cosmetics. Thus, a large amount of the powder should be added to the Pickering emulsion to achieve higher emulsion stability. As a result, the high concentration of the powder particles leads to creakiness and powderiness, which tends to result in impairment of fresh feeling. A Pickering emulsion containing spherical organic particles instead of inorganic powder particles as an emulsifying agent is also produced to solve the problem. However, more than a dozen percent, in total, of the spherical organic particles and an elastomeric organopolysiloxane should be added, and thus the problem relating to creakiness and powderiness is not sufficiently solved under current circumstances (see Patent Literature 5).

CITATION LIST

Patent Literatures

Patent Literature 1: JP 2656226 B
Patent Literature 2: JP 2001-518111 W
Patent Literature 3: JP 2007-332037 A
Patent Literature 4: JP 2006-36763 A
Patent Literature 5: JP 11-158030 A

Non-Patent Literature

Non-Patent Literature 1: B. Binks et. al, Advances in Colloid and Interface Science, 100-102 (2003).

As described above, a Pickering emulsion produced without using a surfactant has insufficient emulsion stability. When the amount of a powder used is increased or an amphiphilic substance is made to coexist in order to improve the stability, the resultant emulsion has creakiness and stickiness, leading to a problem of impairing fresh feeling which is a favorable property of the emulsion composition.

SUMMARY OF THE INVENTION

Technical Problems

The present invention has been made in view of the problems as mentioned above. An object of the present invention is to provide, without use of a surfactant, an oil-in-water emulsion composition and cosmetics having fresh and smooth feeling without powderiness in use, and having excellent emulsion stability by preparing a Pickering emulsion using a spherical polylactic acid powder.

Solution to Problems

The inventors, after pursuing a diligent study to achieve the above object, have found that an oil-in-water emulsion composition, which is obtained by addition of a spherical polylactic acid powder having a specific particle size distribution, has excellent emulsion stability, and has fresh and smooth feeling without stickiness, creakiness, and powderiness in use, and thus accomplished the present invention.

Therefore, an oil-in-water emulsion composition according to a first invention contains:

(a) a spherical polylactic acid powder having an average particle size of from 0.5 to 1.5 µm, wherein 90% by volume or more of the whole particles of the powder have a particle size of 3 µm or less, (b) an oil phase component, and (c) an aqueous phase component.

In the above case, the composition can contain substantially no surfactant.

Further, the composition can contain from 1.0 to 50.0% by mass of the spherical polylactic acid powder of the above component (a).

Then, cosmetics according to a fourth invention contain:

the oil-in-water emulsion composition according to the first invention, the second invention, or the third invention.

Advantageous Effects of Invention

The oil-in-water emulsion composition provided according to the present invention contains (a) a spherical polylactic acid powder having an average particle size of from 0.5 to 1.5 µm, wherein 90% by volume or more of the whole particles of the powder have a particle size of 3 µm or less, (b) an oil phase component, and (c) an aqueous phase component, and thus is an oil-in-water emulsion composition having excellent emulsion stability. The above oil-in-water emulsion composition contains substantially no surfactant, and has pleasant fresh and smooth feeling without stickiness, creakiness, and powderiness in use. Cosmetics having excellent emulsion stability can be obtained by using the above oil-in-water emulsion composition.

DESCRIPTION OF EMBODIMENT

Figure 1:
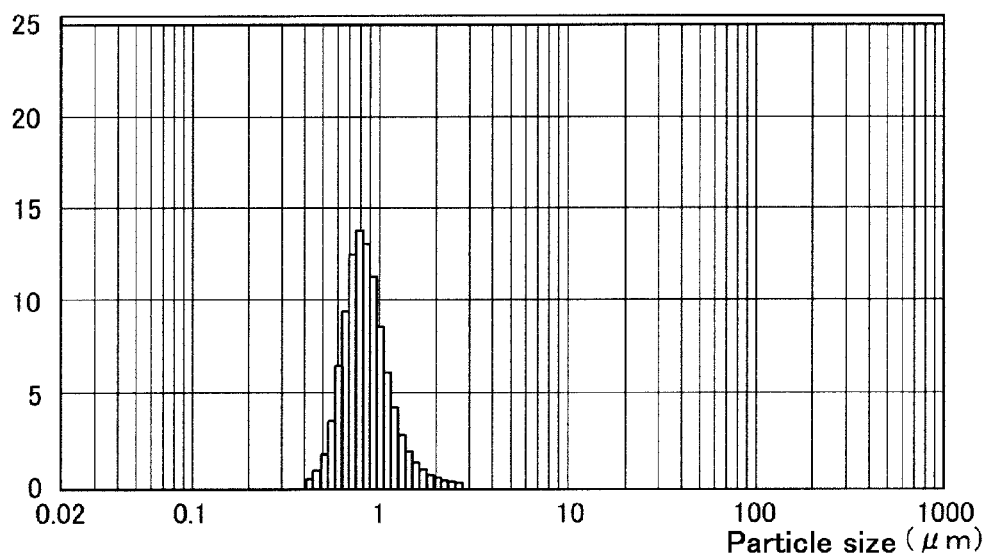
FIG. 1 is a graph showing a result obtained from measurement of volume average particle size of a spherical polylactic acid powder according to the manufacturing example using a laser diffraction particle size distribution analyzer.

Description of an embodiment of an oil-in-water emulsion composition and cosmetics according to the present invention is provided below.

An oil-in-water emulsion composition according to the present invention contains a spherical polylactic acid powder (a spherical biodegradable polymer powder), an oil phase, and an aqueous phase, and can be manufactured by a conventional method.

A spherical polylactic acid powder of the component (a) according to the present invention has an average particle size of from 0.5 to 1.5 μm, and 90% by volume or more of the whole particles of the powder have a particle size of 3 μm or less. The spherical polylactic acid powder can be manufactured by steps of (1) to (3) provided below.

(1) Melt mixing a water-insoluble polylactic acid with a polyglycerin fatty acid ester.

(2) Melt dispersing the above mixture of (1) in a water-soluble material.

(3) Washing the above mixture of (2) with water to remove a water-soluble material.

Examples of the polyglycerin fatty acid ester, which can be used for producing a spherical polylactic acid powder, can be selected from the group consisting of polyglyceryl monolaurate, decaglyceryl monomyristate, polyglyceryl monostearate, polyglyceryl monoisostearate, polyglyceryl monooleate, and polyglyceryl diisostearate. The polyglycerin fatty acid esters can be used solely, or two or more of the polyglycerin fatty acid esters can be used in combination. The amount of the polyglycerin fatty acid ester added is, as a ratio of polylactic acid:polyglycerin fatty acid ester, preferably in a range of from 99.5:0.5 to 95:5, more preferably in a range of from 99:1 to 97:3. When the amount of a polyglycerin fatty acid ester added is, as a ratio of polylactic acid:polyglycerin fatty acid ester, out of the range of from 99.5:0.5 to 95:5, the average particle size of the obtained spherical polylactic acid powder is larger than 1.5 μm, and thus a desired spherical polylactic acid powder cannot be obtained.

Examples of the water-soluble material include polyalkylene oxides such as polyethylene glycol, and polyalkene carboxylic acids such as polyacrylic acid. A homopolymer or a copolymer of the materials, or even a salt thereof can be used. One of the above materials can be used solely, or two or more of the above materials can be used in combination.

In a manufacturing method of the spherical polylactic acid powder, apparatuses used for melt mixing and melt dispersing include, but are not specifically limited to, a roller, a Banbury mixer, a kneader, an extruder, and the like.

Methods for removing the water-soluble material include separation by centrifugation and filtration. The separated spherical polylactic acid powder can be dried before use as desired.

Preferably, the spherical polylactic acid powder of the component (a) according to the present invention has an average particle size of from 0.5 to 1.5 μm, wherein 90% by volume or more of the whole particles of the powder have a particle size of 3 μm or less. When the average particle size is within the above range, a stable oil-in-water emulsion composition can be obtained. When the average particle size is smaller than 0.5 μm, it is concerned that decreased production efficiency can increase the cost. On the contrary, when the average particle size is larger than 1.5 μm, an oil-in-water emulsion composition cannot be obtained. Further, with respect to sphericity of the spherical polylactic acid powder, a ratio of the maximum radius to the minimum radius of the sphere (maximum radius/minimum radius) is preferably in the range of from 1.0 to 1.5.

Examples of the measurement method for particle size of the spherical polylactic acid powder include a method of determination from an image acquired from a microphotograph obtained by electron microscope observation, and a method of measurement with a particle size distribution measurement apparatus such as a laser diffraction particle size distribution analyzer. The measurement method with a laser diffraction particle size distribution analyzer is preferably used.

Various surface treatments conventionally known per se can be applied to the spherical polylactic acid powder. Examples of the surface treatment include the treatments provided below. Two or more of the treatments can be used in combination. A natural material is preferably used in view of environmental load. Such treatments include the following:

a) a fluorine compound treatment: a perfluoro alkyl phosphoric acid ester treatment, a perfluoro alkyl silane treatment, a perfluoropolyether treatment, a fluoro silicone treatment, a fluorinated silicone resin treatment, and the like, b) a silicone treatment: a methyl hydrogen polysiloxane treatment, a dimethyl polysiloxane treatment, a gas-phase tetramethyl tetrahydrogen cyclotetrasiloxane treatment, and the like, c) a pendant treatment: a gas-phase silicone treatment, which is followed by a treatment of adding an alkyl chain, and the like, d) a silane coupling agent treatment, e) a titanium coupling agent treatment, f) an aluminum coupling agent treatment, g) an oil agent treatment, h) an N-acylated lysine treatment, i) a polyacrylic acid treatment, j) a metallic soap treatment: a stearic acid salt treatment, a myristic acid salt treatment, and the like, k) an acrylic resin treatment, and l) a metal oxide treatment.

In the oil-in-water emulsion composition of the present invention, the amount of the spherical polylactic acid powder, i.e., the component (a) added is from 1.0 to 50.0% by mass of the whole emulsion composition, particularly preferably from 5.0 to 25.0% by mass. When the amount is below 1.0% by mass or above 50.0% by mass, an emulsion composition cannot be obtained. When the amount is below 5% by mass, emulsification can be achieved insufficiently. When the amount is above 25% by mass, powderiness tends to be increased.

In the oil-in-water emulsion composition of the present invention, examples of the oil phase component, i.e., the component (b) include a hydrocarbon oil, a higher fatty acid, a higher alcohol, a synthetic ester oil, a silicone oil, a liquid oil and fat, a solid oil and fat, waxes, and the like, which are widely used in cosmetics and quasi-drugs.

Examples of the hydrocarbon oil include isododecane, isohexadecane, isoparaffin, liquid paraffin, ozokerite, squalane, pristane, paraffin, ceresin, squalene, petrolatum, and the like.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), docosahexaenoic acid (DHA), and the like.

Examples of the higher alcohol include linear alcohols (such as lauryl alcohol, cetyl alcohol, stearyl alcohol, behenyl alcohol, myristyl alcohol, oleyl alcohol, and cetostearyl alcohol), branched alcohols (such as monostearyl glycerin ether (batyl alcohol)-2-decyltetradecynol, lanolin alcohol, cholesterol, phytosterol, hexyldodecanol, isostearyl alcohol, and octyldodecanol), and the like.

Examples of the synthetic ester oil include octyl octanoate, nonyl nonanoate, cetyl octanoate, isopropyl myristate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethyl hexanoate, a dipentaerythritol fatty acid ester, N-alkyl glycol monoisostearate, neopentylglycol dicaprate, tripropylene glycol pivalate, diisostearyl malate, glycerin di-2-heptyl undecanoate, glycerin diisostearate, trimethylolpropane tri-2-ethyl hexanoate, trimethylolpropane triisostearate, pentaerythritol tetra-2-ethyl hexanoate, glycerin tri-2-ethyl hexanoate, glycerin trioctanoate, glycerin triisopalmitate, trimethylolpropane triisostearate, cetyl 2-ethyl hexanoate-2-ethyl hexyl palmitate, glycerin trimyristate, glyceride tri-2-heptyl undecanoate, a castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, and the like.

Examples of the silicone oil include linear polysiloxanes (e.g., dimethyl polysiloxane, methyl phenyl polysiloxane, and diphenyl polysiloxane), cyclic polysiloxanes (e.g., octamethyl cyclotetrasiloxane, decamethyl cyclopentasiloxane, a dodecamethyl cyclohexasiloxane), a 3D network-structured silicone resin, a silicone rubber, various modified polysiloxanes (an amino-modified polysiloxane, a polyether-modified polysiloxane, an alkyl-modified polysiloxane, a fluorine-modified polysiloxane, and the like), acrylic silicones, and the like.

Examples of the liquid oil and fat include avocado oil, camellia oil, turtle oil, macadamia nut oil, corn oil, mink oil, rice oil, olive oil, rape oil, egg-yolk oil, sesame oil, persic oil, wheat-germ oil, camellia oleifera seed oil, castor oil, linseed oil, safflower oil, cottonseed oil, perilla oil, soybean oil, peanut oil, tea seed oil, kaya oil, rice-bran oil, Chinese tung oil, Japanese tung oil, jojoba oil, germ oil-triglycerol, and the like.

Examples of the solid oil and fat include cacao butter, coconut fat, horse fat, hardened coconut oil, palm oil, beef tallow, mutton tallow, hardened beef fat, palm kernel oil, lard, beef bone fat, sumac seed oil, hydrogenated oil, neat's-foot oil, sumac wax, hydrogenated castor oil, and the like.

Examples of the waxes include beeswax, candelilla wax, cotton wax, carnauba wax, bayberry wax, Ericerus pela wax, spermaceti wax, montan wax, rice bran wax, lanolin, kapok wax, lanolin acetate, liquid lanolin, sugarcane wax, a lanolin fatty acid isopropyl, hexyl laurate, hydrogenated lanolin, jojoba wax, hard lanolin, shellac wax, POE lanolin alcohol ether, POE lanolin alcohol acetate, POE cholesterol ether, a lanolin fatty acid polyethylene glycol, POE hydrogenated lanolin alcohol ether, and the like.

In the oil-in-water emulsion composition of the present invention, water (purified water, ion-exchanged water, tap water, and the like), a water-soluble alcohol, a thickener, and the like, which are generally used in cosmetics, a quasi-drug, and the like, can be added as the aqueous phase component, i.e., the component (c). Further, a humectant, a chelating agent, an antiseptic, a dye, and the like can be added as desired.

Examples of the water-soluble alcohol include one or more of lower alcohols, polyalcohols, polyalcohol polymers, diol alkyl ethers, diol ether esters, glycerin monoalkyl ethers, sugar alcohols, monosaccharides, oligosaccharides, polysaccharides, and derivatives of the above alcohols.

Examples of the lower alcohol include ethanol, propanol, isopropanol, isobutyl alcohol, t-butyl alcohol, and the like.

Examples of the polyalcohol include diols (e.g., dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol), triols (e.g., glycerol and trimethylolpropane), tetrols (e.g., pentaerythritols, such as diglycerol and 1,2,6-hexane triol), pentols (e.g., xylitol and triglycerol), hexols (e.g., sorbitol and mannitol), polyalcohol polymers (e.g., diethylene glycol, dipropylene glycol-triethylene glycol, polypropylene glycol, tetraethylene glycol, diglycerol-triglycerol, tetraglycerol, and polyglycerol), diol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether), diol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate), glycerin monoalkyl ethers (e.g., chimyl alcohol, selachyl alcohol, and batyl alcohol), sugar alcohols (e.g., maltotriose, mannitol, saccharose, erythritol, glucose, fructose, a starch sugar, maltose, and a starch sugar hydrogenated alcohol), glysolid, tetrahydrofurfuryl alcohol, POE-tetrahydrofurfuryl alcohol, POP-butyl ether, POP/POE-butyl ether tripolyoxypropylene glycerin ether, POP-glycerin ether, POP-glycerin ether phosphoric acid, POP/POE-pentane erythritol ether, polyglycerol, and the like.

Examples of the monosaccharide include trioses (e.g., D-glyceraldehyde and dihydroxy acetone), tetroses (e.g., D-erythrose, D-erythrulose, D-threose, and erythritol), pentoses (e.g., L-arabinose, D-xylose, L-lyxose, D-arabinose, D-ribose, D-ribulose, D-xylulose, and L-xylulose), hexoses (e.g., D-glucose, D-talose, D-psicose, D-galactose, D-fructose, L-galactose, L-mannose, and D-tagatose), heptoses (e.g., aldoheptose and heplose), octoses (e.g., octlose), deoxy sugars (e.g., 2-deoxy-D-ribose, 6-deoxy-L-galactose, and 6-deoxy-L-mannose), amino sugars (e.g., D-glucosamine, D-galactosamine, sialic acid, aminouronic acid, and muramic acid), uronic acids (e.g., D-glucuronic acid, D-mannuronic acid, L-guluronic acid, D-galacturonic acid, and L-iduronic acid), and the like.

Examples of the oligosaccharide include saccharose, guntianose, umbelliferose, lactose, planteose, isolychnoses, α,α-trehalose, raffinose, lychnoses, umbilicin, stachyose, verbascoses, and the like.

Examples of the polysaccharide include cellulose, quince seed, starch, galactan, dermatan sulfate, glycogen, gum arabic, heparan sulfate-tragacanth gum, keratan sulfate, chondroitin, xanthan gum, guar gum, dextran, keratosulfate, locust bean gum, succinoglucan, and the like.

Examples of other polyols include polyoxyethylene methyl glucoside (Glucam E-10), polyoxypropylene methyl glucoside (Glucam P-10), and the like.

Examples of the thickener include gum arabic, carrageenan, karaya gum, tragacanth gum, carob gum, quince seed (marmelo), casein, dextrin, gelatin, sodium pectate, sodium alginate, methyl cellulose, ethyl cellulose, CMC, hydroxyethyl cellulose, hydroxy propyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, aluminum magnesium silicate (VEEGUM), bentonite, hectorite, LAPONITE, silicic anhydride, and the like.

Examples of a natural water-soluble polymer include plant polymers (e.g., gum arabic, tragacanth gum, galactan, guar gum, carob gum, karaya gum, carrageenan, pectin, agar, quince seed (marmelo), algae colloid (brown algae extract), starch (rice, corn, potato, wheat), and glycyrrhizic acid), microbial polymers (e.g., xanthan gum, dextran, succinoglucan, and pullulan), animal polymers (e.g., collagen, casein, albumin, and gelatin), and the like.

Examples of a semi-synthetic water-soluble polymer include starch polymers (e.g., carboxymethyl starch and methyl hydroxy propyl starch), cellulose polymers (e.g., methyl cellulose, ethyl cellulose, methyl hydroxy propyl cellulose, hydroxyethyl cellulose, cellulose sodium sulfate, hydroxy propyl cellulose, carboxymethyl cellulose, carboxymethyl cellulose sodium, crystalline cellulose, and cellulose powder), alginic acid polymers (e.g., sodium alginate and alginic acid propylene glycol ester), and the like.

Examples of a synthetic water-soluble polymer include vinyl polymers (e.g., polyvinyl alcohol, polyvinyl methyl ether, polyvinyl pyrrolidone, and a carboxyvinyl polymer), polyoxyethylene polymers (e.g., polyethylene glycol 20,000, 40,000, and 60,000), acrylic polymers (e.g., sodium polyacrylate, polyethyl acrylate, and polyacrylamide), polyethylenimine, a cation polymer, and the like.

Examples of the humectant include chondroitin sulfate, hyaluronic acid, mucoitin sulfate, charonic acid, atelocollagen, cholesteryl-12-hydroxy stearate, sodium lactate, bile salt, DL-pyrrolidone carboxylic acid, short chain soluble collagen, diglycerol (EO)-PO adduct, chestnut rose extract, common yarrow extract, melilot extract, and the like.

Examples of a sequestering agent include 1-hydroxyethane-1,1-diphosphonic acid, 1-hydroxyethane-1,1-diphosphonic acid tetrasodium salt, edetate disodium, edetate trisodium, edetate tetrasodium, sodium citrate, sodium polyphosphate, sodium metaphosphate, gluconic acid, phosphoric acid, citric acid, ascorbic acid, succinic acid, edetic acid, trisodium ethylenediamine hydroxyethyl triacetate, and the like.

Examples of an amino acid include neutral amino acids (e.g., threonine and cysteine), basic amino acids (e.g., hydroxy lysine), and the like. Further, examples of an amino acid derivative include acyl sarcosine sodium (lauroyl sarcosine sodium), acyl glutamate, acyl β-alanine sodium, glutathione, and the like.

Examples of a pH adjustor include buffers, such as lactic acid-sodium lactate, citric acid-sodium citrate, and succinic acid-sodium succinate, and the like.

In the oil-in-water emulsion composition according to the present invention, an additional component, which is generally used in cosmetics, a quasi-drug, and the like, can be used along with the above essential components. The oil-in-water emulsion composition according to the present invention can be applied to oil-in-water emulsion cosmetics, such as makeup cosmetics, skin care cosmetics, and hair cosmetics, and can have various dosage forms and product forms depending on purposes. The dosage forms include a liquid form, a milk form, a cream form, and the like. The product forms include a milky lotion, a sun protect milky lotion, a foundation, a cream, a sun protect cream, a cleansing cream, a hair cream, and the like.

EXAMPLES

The present invention is described below in detail for better understanding with reference to examples in connection with oil-in-water emulsion compositions and cosmetics according to the present invention, but it should not be construed to be limited to the examples in any way. In the examples, any "%" refers to "% by mass".

First, a manufacturing example of a spherical polylactic acid powder used in the present invention and a comparative manufacturing example are described below.

Manufacturing Example: A Spherical Polylactic Acid Powder Having an Average Particle Size of from 0.5 to 1.5 μm To 98 parts by mass of a polylactic acid (manufactured by UNITIKA LTD., TERRAMAC TP-4000CN) was added 2 parts by mass of polyglyceryl-5 laurate (manufactured by Taiyo Kagaku Co., Ltd., Sunsoft A-121E-C). The resultant was thoroughly mixed, and then the mixture was supplied to a feed port of a co-rotating twin-screw extruder (manufactured by THE JAPAN STEEL WORKS, LTD., TEX30α). The mixture was melt mixed by heating the cylinder of the extruder to 180° C., and then the resin composition was extruded from the nozzle to cool and solidify. Further, to 33 parts by mass of the obtained resin composition was added 67 parts by mass of polyacrylic acid (manufactured by Toagosei Co., Ltd., JURYMER AC-10P). The resultant was thoroughly mixed, and then the mixture was supplied to the feed port of the co-rotating twin-screw extruder (manufactured by THE JAPAN STEEL WORKS, LTD., TEX30α). The mixture was melt dispersed by heating the cylinder of the extruder to 180° C., and then the resin composition was extruded from the nozzle to cool and solidify. Then, the polyacrylic acid was dissolved with 10 times as much water by mass as the obtained resin composition, so that a suspension of a spherical polymer powder of the polylactic acid was obtained. The suspension was filtered, and then dried to give a desired spherical polylactic acid powder.

Comparative Manufacturing Example: A Spherical Polylactic Acid Powder Having an Average Particle Size of from 5 to 9 μm To 40 parts by mass of a polylactic acid (manufactured by UNITIKA LTD., TERRAMAC TP-4000CN) as a water-insoluble biodegradable polymer was added 60 parts by mass of polyacrylic acid (manufactured by Toagosei Co., Ltd., JURYMER AC-10P). The resultant was thoroughly mixed, and then the mixture was supplied to a feed port of a co-rotating twin-screw extruder (manufactured by THE JAPAN STEEL WORKS, LTD., TEX30α). The mixture was melt dispersed by heating the cylinder of the extruder to 180° C., and then the resin composition was extruded from the nozzle to cool and solidify. Then, the polyacrylic acid was dissolved with 10 times as much water by mass as the obtained resin composition, so that a suspension of a spherical biodegradable polymer powder of the polylactic acid was obtained. The suspension was filtered, and then dried to give the spherical polylactic acid powder of the comparative manufacturing example.

(Average Particle Size of the Spherical Polylactic Acid Powders)

Figure 2:
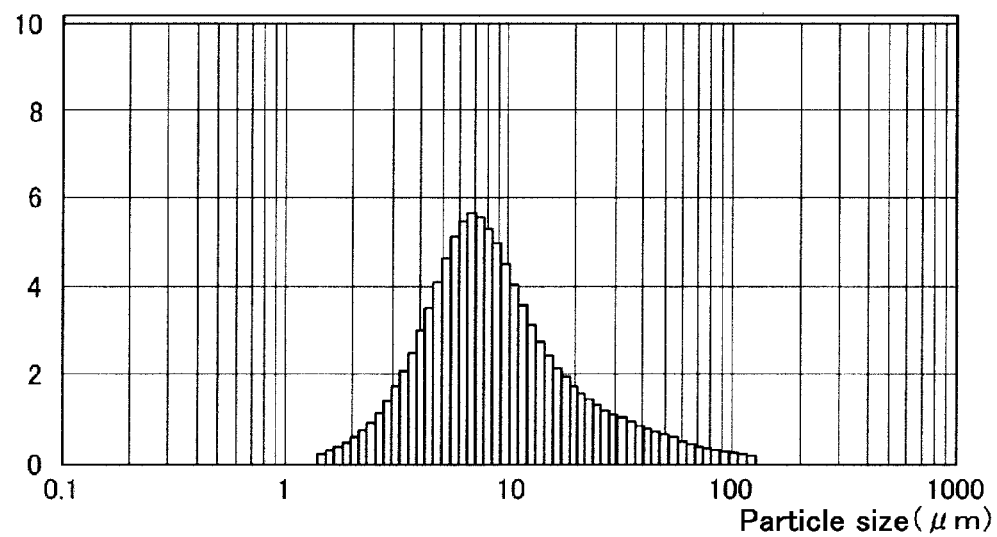
FIG. 2 is a graph showing a result obtained from measurement of volume average particle size of a spherical polylactic acid powder according to the comparative manufacturing example using a laser diffraction particle size distribution analyzer.

Volume average particle sizes of spherical polylactic acid powders of the manufacturing example and the comparative manufacturing example were measured with a laser diffraction particle size distribution analyzer (manufactured by NIKKISO CO., LTD., Microtrac MT3300EXII). Obtained results of the measurement with the laser diffraction particle size distribution analyzer were as follows. With respect to the powder of the manufacturing example, the obtained average particle size was 0.8 μm, wherein 90% by volume or more of the whole particles of the powder had a particle size of 3 μm or less as shown in FIG. 1. With respect to the powder of the comparative manufacturing example, the obtained average particle size was 7.6 μm as shown in FIG. 2.

Next, examples of the oil-in-water emulsion composition according to the present invention are described below.

First, an evaluation method used in the examples is described below.

Evaluation (1): Emulsion Stability (Appearance)

An appearance of an emulsion was observed with naked eye within one day after preparation of the emulsion.

◯: The sample was homogeneous, and no water separation and powder aggregation were observed.

Δ: The sample was mostly homogeneous, but slight water separation was observed.

x: The sample was not homogeneous, or significant separation of an aqueous phase or powder aggregation was observed.

Evaluation (2): Emulsion Stability (Emulsified Particles)

The sample was observed with an optical microscope.

◯: The emulsified particles were homogeneous, and no coalescence and aggregation were observed.

Δ: The emulsified particles were mostly homogeneous, but slight coalescence and aggregation were observed.

x: The emulsified particles were not homogeneous, and significant coalescence and aggregation were observed.

Example 1 and Comparative Examples 1 to 5

Oil-in-water emulsion compositions having the compositions shown in Table 1 were prepared, and then each sample of the compositions was tested for evaluation with respect to the above Evaluations (1) and (2). The compositions were prepared by a method of emulsifying a mixture while an oil phase was gradually added to an aqueous phase in which a powder was dispersed.

TABLE 1

|  | Example 1 | Comparative Example 1 | Comparative Example 2 | Comparative Example 3 | Comparative Example 4 | Comparative Example 5 |
|---|---|---|---|---|---|---|
| Purified water | q.s. | q.s. | q.s. | q.s. | q.s. | q.s. |
| Isopropyl isostearate | 45.0 | 45.0 | 45.0 | 45.0 | 45.0 | 45.0 |
| Spherical polylactic acid powder of Manufacturing Example | 15.0 | — | — | — | — | — |
| Spherical polylactic acid powder of Comparative Manufacturing Example | — | 15.0 | — | — | — | — |
| Spherical cellulose powder 1*[1] | — | — | 15.0 | — | — | — |
| Spherical cellulose powder 2*[2] | — | — | — | 15.0 | — | — |
| Spherical polymethyl methacrylate resin powder 1*[3] | — | — | — | — | 15.0 | — |
| Spherical polymethyl methacrylate resin powder 2*[4] | — | — | — | — | — | 15.0 |
| Evaluation (1) appearance | ◯ | x | x | x | x | x |
| Evaluation (2) emulsified particles | ◯ | x | x | x | x | x |

*[1] Porous spherical cellulose powder having an average particle size of 4 μm
*[2] Spherical cellulose powder having an average particle size of 10 μm or less
*[3] Spherical polymethyl methacrylate resin powder having an average particle size of 6 μm
*[4] Porous spherical polymethyl methacrylate resin powder having an average particle size of 7 μm In Example 1 in which a spherical polylactic acid powder (Manufacturing Example) of the component (a), which was a product according to the present invention, was used, it was possible to prepare an oil-in-water emulsion composition having favorable emulsion stability. On the other hand, in Comparative Examples 1 to 5 in which a spherical powder which was different from the spherical polylactic acid powder (Manufacturing Example) of the component (a) according to the present invention was used, it was impossible to emulsify the composition.

Then, description of an oil-in-water milky lotion (Example 2), oil-in-water sunscreen milky lotions (Examples 3 and 4), and oil-in-water liquid foundations (Examples 5 and 6) as cosmetics containing oil-in-water emulsion compositions are provided below.

Example 2: Oil-in-Water Milky Lotion

TABLE 2

|  | Example 2 |
|---|---|
| <Oil phase component> | |
| Rice oil | 25.0 |
| <Aqueous phase component> | |
| Purified water | q.s. |
| 1,3-Butylene glycol | 4.0 |
| Phenoxy ethanol | 0.1 |
| Alcohol | 25.0 |
| Spherical polylactic acid powder of Manufacturing Example | 15.0 |

<Production Method>

An oil-in-water milky lotion was obtained by a preparation method the same as that of Example 1.

Example 3: Oil-in-Water Sunscreen Milky Lotion

TABLE 3

|  | Example 3 |
|---|---|
| <Oil phase component> | |
| Decamethyl cyclopentasiloxane | 8.00 |
| Isononyl isononanoate | 5.00 |
| Octyl methoxycinnamate | 5.00 |
| <Aqueous phase component> | |
| Ethanol | 25.00 |
| Spherical polylactic acid powder of Manufacturing Example | 10.00 |
| 50% aqueous dispersion of titanium dioxide*[1] | 10.00 |
| Glycerol | 3.00 |
| 10% aqueous sodium hydroxide | 0.70 |
| Carbomer | 0.20 |
| Antiseptic | Proper amount |
| Purified water | q.s. |

*[1]Daitopersion Ti-50WN (manufactured by DAITO KASEI KOGYO CO., LTD.)

<Production Method>

An oil-in-water sunscreen milky lotion was obtained by dispersing an aqueous phase with a mixer or by ultrasonication, then adding an oil phase to the resultant dispersion, and emulsifying the resultant mixture using an emulsifier.

Example 4: Oil-in-Water Sunscreen Milky Lotion

TABLE 4

|  | Example 4 |
|---|---|
| <Oil phase component> | |
| Decamethyl cyclopentasiloxane | 8.00 |
| Isopropyl isostearate | 5.00 |
| Octyl methoxycinnamate | 5.00 |
| <Aqueous phase component> | |
| Spherical polylactic acid powder of Manufacturing Example | 10.00 |
| Hydrophilic treated titanium dioxide*[1] | 10.00 |
| Glycerol | 3.00 |
| Sodium chloride | 1.00 |
| Xanthan gum | 0.15 |
| Antiseptic | Proper amount |
| Purified water | q.s. |

*[1]SIH-10 UFTi80 (manufactured by DAITO KASEI KOGYO CO., LTD.)

<Production Method>

An oil-in-water sunscreen milky lotion was obtained by dispersing an aqueous phase with a mixer or by ultrasonication, then adding an oil phase to the resultant dispersion, and emulsifying the resultant mixture using an emulsifier.

Example 5: Oil-in-Water Liquid Foundation

TABLE 5

|  | Example 5 |
|---|---|
| <Oil phase component> | |
| Decamethyl cyclopentasiloxane | 8.00 |
| Phytosqualane | 5.00 |
| Octyl methoxycinnamate | 5.00 |
| Aqueous phase component> | |
| Ethanol | 25.00 |
| 1,3-Butylene glycol | 4.00 |
| Glycerol | 2.00 |
| Edetic acid salt | 0.05 |
| Xanthan gum | 0.20 |
| Antiseptic | Proper amount |
| Spherical polylactic acid powder of Manufacturing Example | 10.00 |
| Hydrophilic treated titanium dioxide*[1] | 10.00 |
| Hydrophilic treated yellow ferric oxide*[2] | 0.80 |
| Hydrophilic treated red iron oxide*[3] | 0.36 |
| Hydrophilic treated black iron oxide*[4] | 0.16 |
| Purified water | q.s. |

*[1]SIH-5 TiO2 R250 (manufactured by DAITO KASEI KOGYO CO., LTD.)
*[2]SIH-2 YELLOW No. 602P (manufactured by DAITO KASEI KOGYO CO., LTD.)
*[3]SIH-2 RED No. 211P (manufactured by DAITO KASEI KOGYO CO., LTD.)
*[4]SIH-2 BLACK No. 710P (manufactured by DAITO KASEI KOGYO CO., LTD.)

<Production Method>

An oil-in-water liquid foundation was obtained by dispersing an aqueous phase with a mixer or by ultrasonication, then adding an oil phase to the resultant dispersion, and emulsifying the resultant mixture using an emulsifier.

Example 6: Oil-in-Water Liquid Foundation

TABLE 6

|  | Example 6 |
|---|---|
| <Oil phase component> | |
| Decamethyl cyclopentasiloxane | 8.00 |
| Phytosqualane | 5.00 |
| Octyl methoxycinnamate | 5.00 |
| <Aqueous phase component> | |
| 1,3-Butylene glycol | 2.00 |
| Glycerol | 4.00 |
| Magnesium sulfate | 1.00 |
| Sodium chloride | 1.00 |
| Xanthan gum | 0.20 |
| Antiseptic | Proper amount |
| Spherical polylactic acid powder of Manufacturing Example | 10.00 |
| Hydrophilic treated titanium dioxide | 10.00 |
| Hydrophilic treated yellow ferric oxide | 0.80 |
| Hydrophilic treated red iron oxide | 0.36 |
| Hydrophilic treated black iron oxide | 0.16 |
| Purified water | q.s. |

<Production Method>

An oil-in-water liquid foundation was obtained by dispersing an aqueous phase with a mixer or by ultrasonication, then adding an oil phase to the resultant dispersion, and emulsifying the resultant mixture using an emulsifier.

INDUSTRIAL APPLICABILITY

An oil-in-water emulsion composition according to the present invention contains substantially no surfactant, and can provide cosmetics having excellent emulsion stability, and fresh and smooth feeling in use. Consequently, the oil-in-water emulsion composition according to the present invention has a significant effect on industrial application.

The invention claimed is:

1. An oil-in-water emulsion composition comprising:
   (a) 1.0 to 50.0% by mass of a spherical polylactic acid powder having an average particle size of from 0.5 to 1.5 μm, wherein 90% by volume or more of whole particles of the powder have a particle size of 3 μm or less,
   (b) an oil phase component, and
   (c) an aqueous phase component.

2. The oil-in-water emulsion composition according to claim 1, wherein the composition does not substantially contain a surfactant.

3. A cosmetic comprising the oil-in-water emulsion composition according to claim 1.

4. The oil-in-water emulsion composition according to claim 2, wherein the spherical polylactic acid powder of the component (a) is contained in an amount of 1.0 to 50.0% by mass.

5. A cosmetic comprising the oil-in-water emulsion composition according to claim 2.

6. A cosmetic comprising the oil-in-water emulsion composition according to claim 4.

7. The oil-in-water emulsion composition according to claim 1, wherein the oil phase component is selected from the group consisting of a hydrocarbon oil, a higher fatty acid, a higher alcohol, a synthetic ester oil, a silicone oil, a liquid oil, a fat, a solid oil and a wax.

8. The oil-in-water emulsion composition according to claim 1, wherein the aqueous phase component comprises water, a water-soluble alcohol and a thickener.

* * * * *